(12) United States Patent
Zweber et al.

(10) Patent No.: US 8,515,558 B1
(45) Date of Patent: Aug. 20, 2013

(54) ANCHORING MECHANISM FOR AN IMPLANTABLE STIMULATION LEAD

(75) Inventors: Jeffrey Zweber, St. Louis Park, MN (US); Jesse Geroy, Ham Lake, MN (US)

(73) Assignee: Greatbatch Ltd., Clarence, NY (US)

( * ) Notice: Subject to any disclaimer, the term of this patent is extended or adjusted under 35 U.S.C. 154(b) by 868 days.

(21) Appl. No.: 12/623,908

(22) Filed: Nov. 23, 2009

Related U.S. Application Data

(60) Provisional application No. 61/116,718, filed on Nov. 21, 2008.

(51) Int. Cl.
*A61N 1/05* (2006.01)

(52) U.S. Cl.
USPC .......................................................... 607/117

(58) Field of Classification Search
USPC .......................................... 600/376; 607/126
See application file for complete search history.

(56) References Cited

U.S. PATENT DOCUMENTS

| | | | |
|---|---|---|---|
| 4,151,835 A * | 5/1979 | Showell et al. | 600/376 |
| 4,217,913 A * | 8/1980 | Dutcher | 607/127 |
| 4,233,992 A * | 11/1980 | Bisping | 607/127 |
| 4,858,623 A | 8/1989 | Bradshaw et al. | |
| 5,425,756 A * | 6/1995 | Heil et al. | 607/128 |
| 5,843,146 A | 12/1998 | Cross | |
| 5,871,532 A | 2/1999 | Schroeppel | |
| 6,473,654 B1 | 10/2002 | Chinn | |
| 6,711,443 B2 | 3/2004 | Osypka | |
| 2007/0078399 A1 | 4/2007 | Olson | |
| 2007/0299493 A1 | 12/2007 | Osypka | |

FOREIGN PATENT DOCUMENTS

| | | |
|---|---|---|
| EP | 1321165 | 6/2003 |
| EP | 1774986 | 4/2007 |

* cited by examiner

*Primary Examiner* — Carl H Layno
*Assistant Examiner* — Luther Behringer
(74) *Attorney, Agent, or Firm* — Michael F. Scalise

(57) ABSTRACT

An improved anchoring mechanism for an implantable lead is discussed. The anchoring mechanism consists of a tine enclosed in a housing structure. Deployment and retraction of the tine is controlled by the rotation of a stylet releasable connected to the tine. The stylet is inserted through the lead and engages the tine at an interface between them. The stylet is rotated. This serves to rotate the tine to thereby secure the lead connected to an anchor housing from which the tine emerges to body tissue.

18 Claims, 8 Drawing Sheets

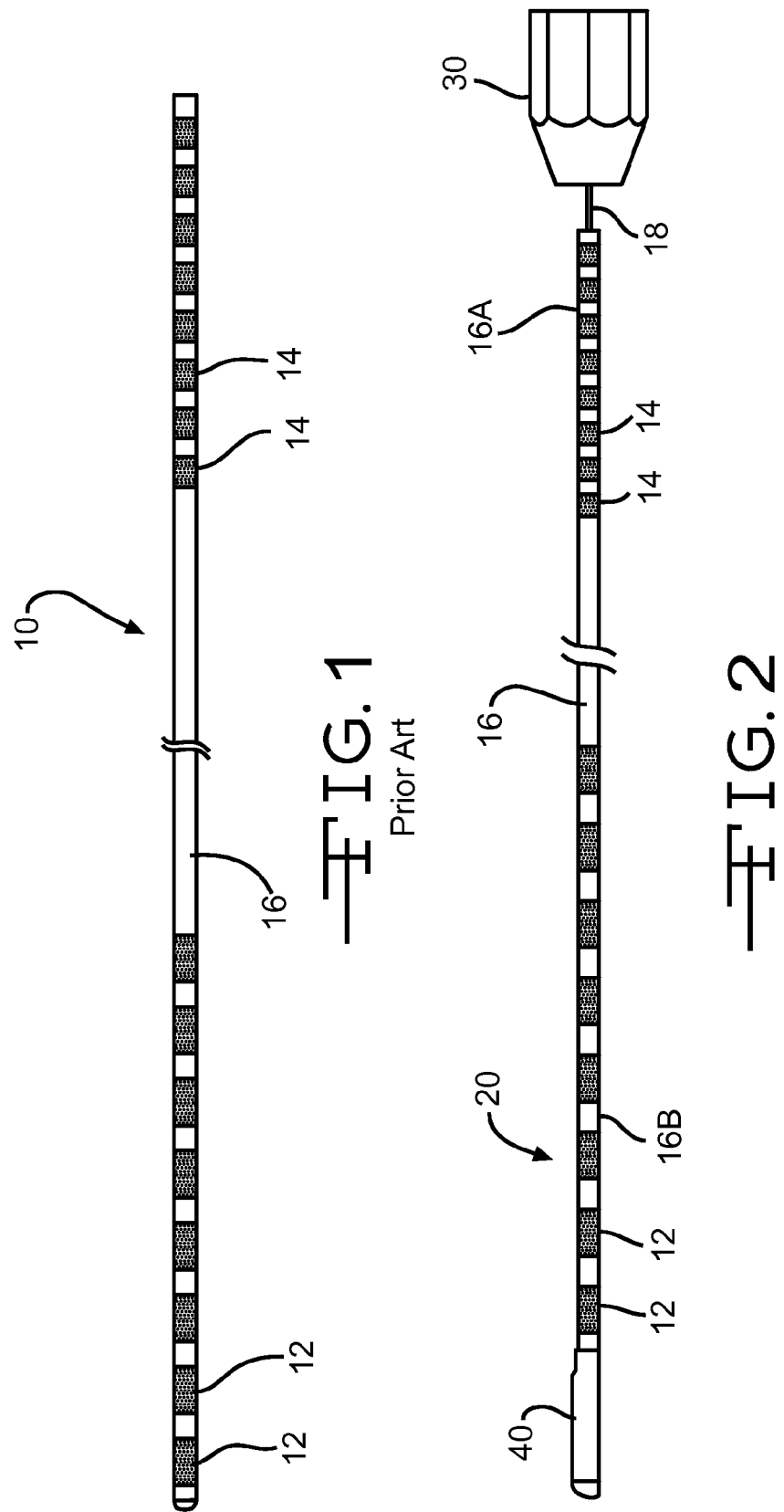

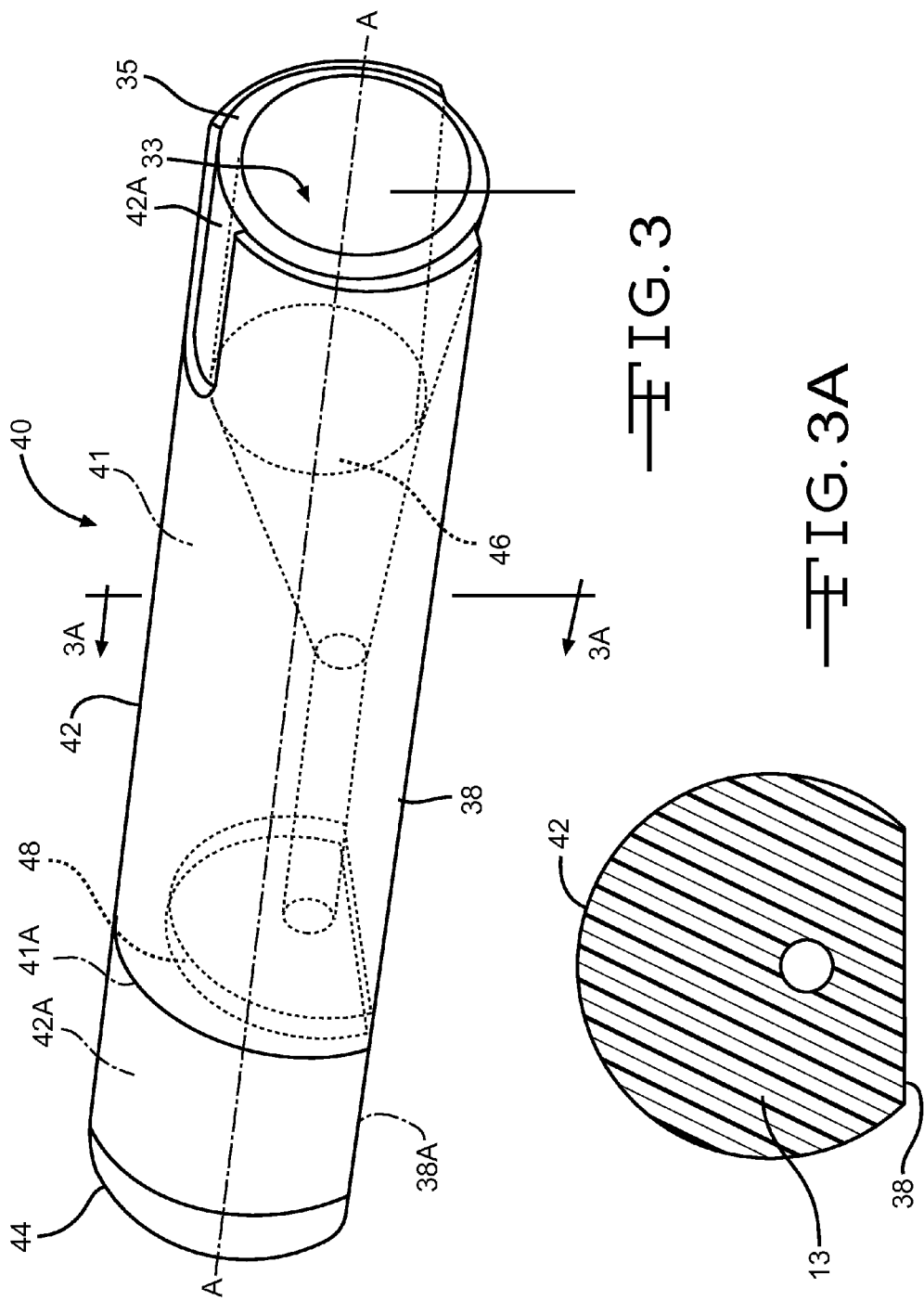

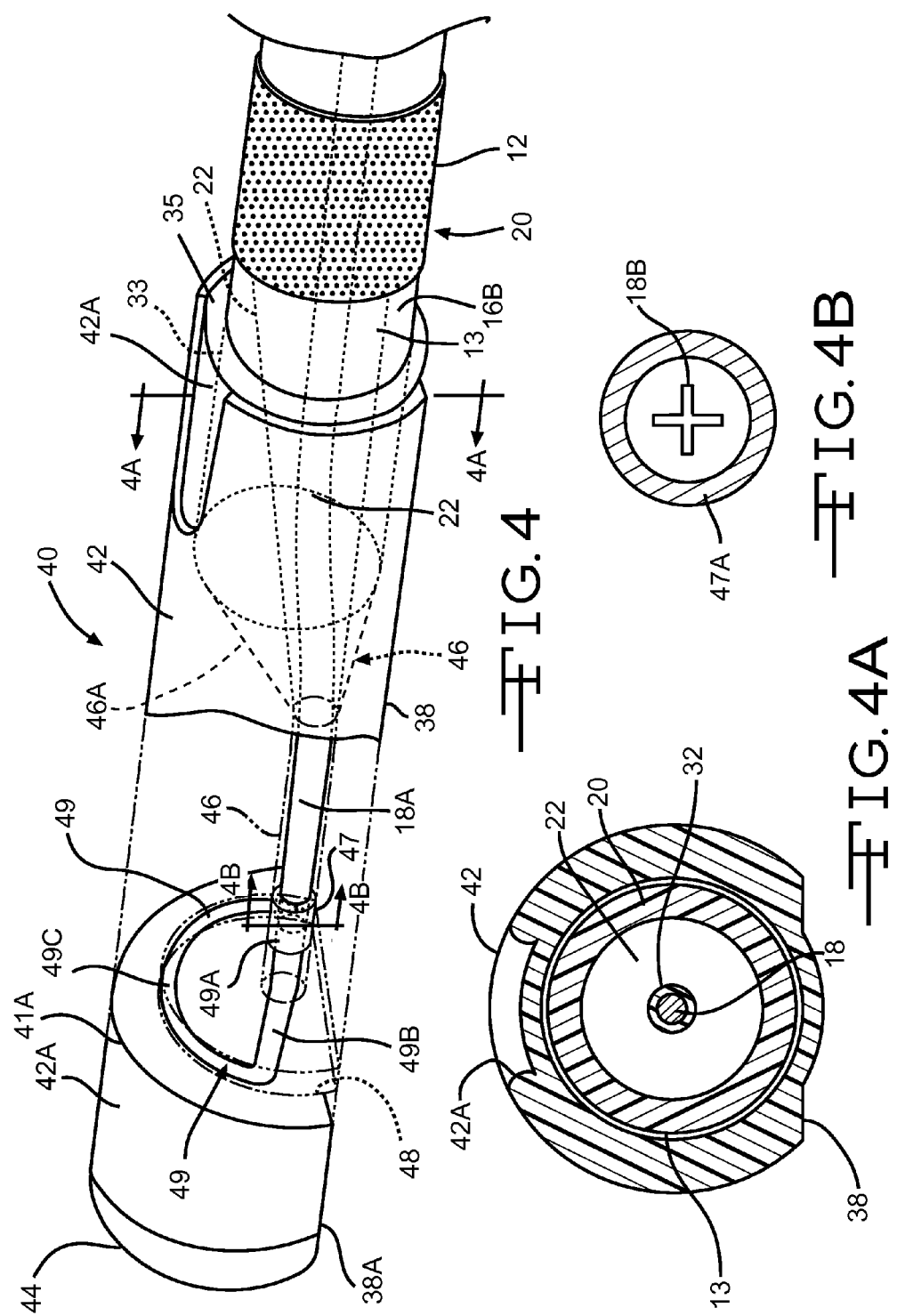

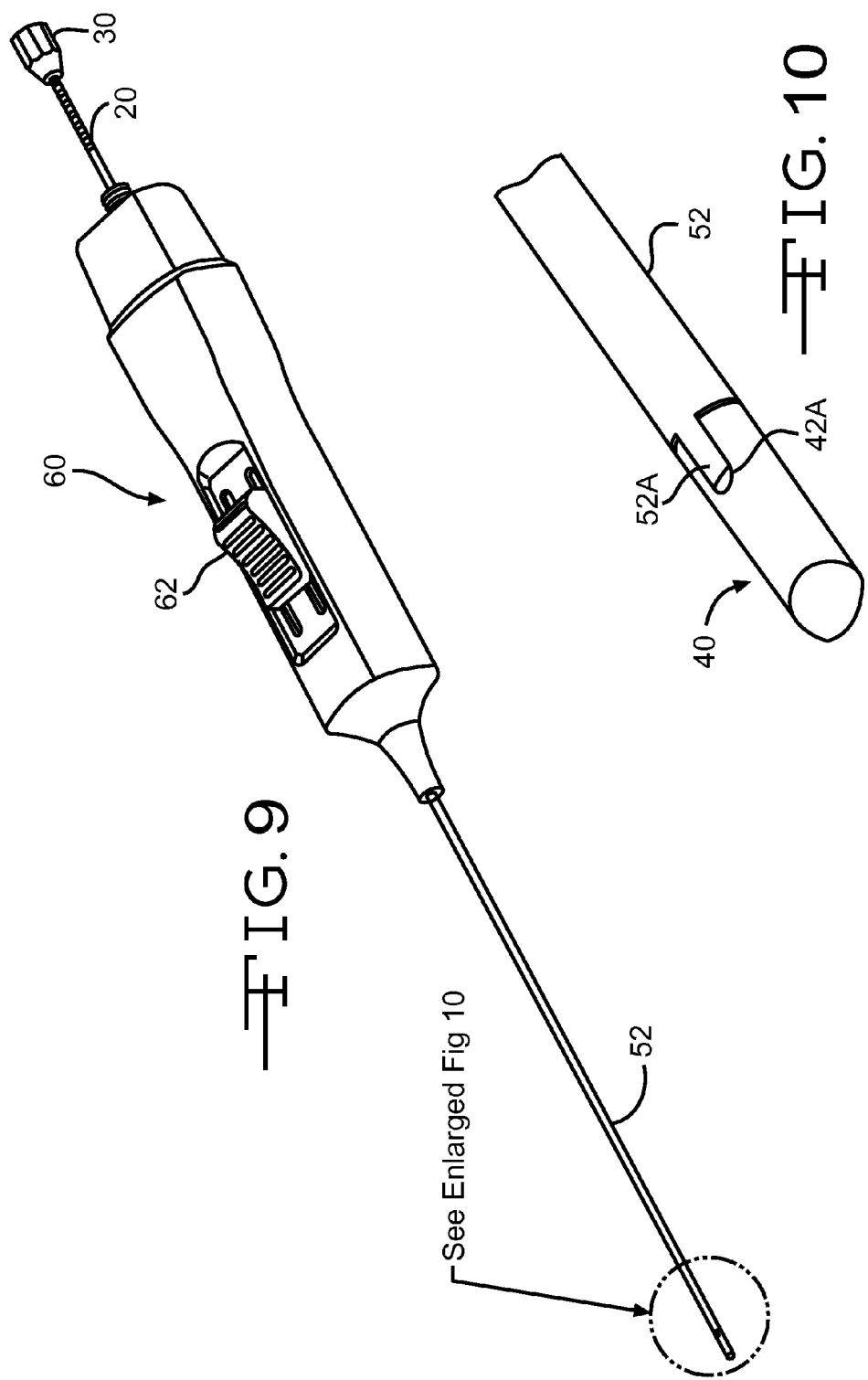

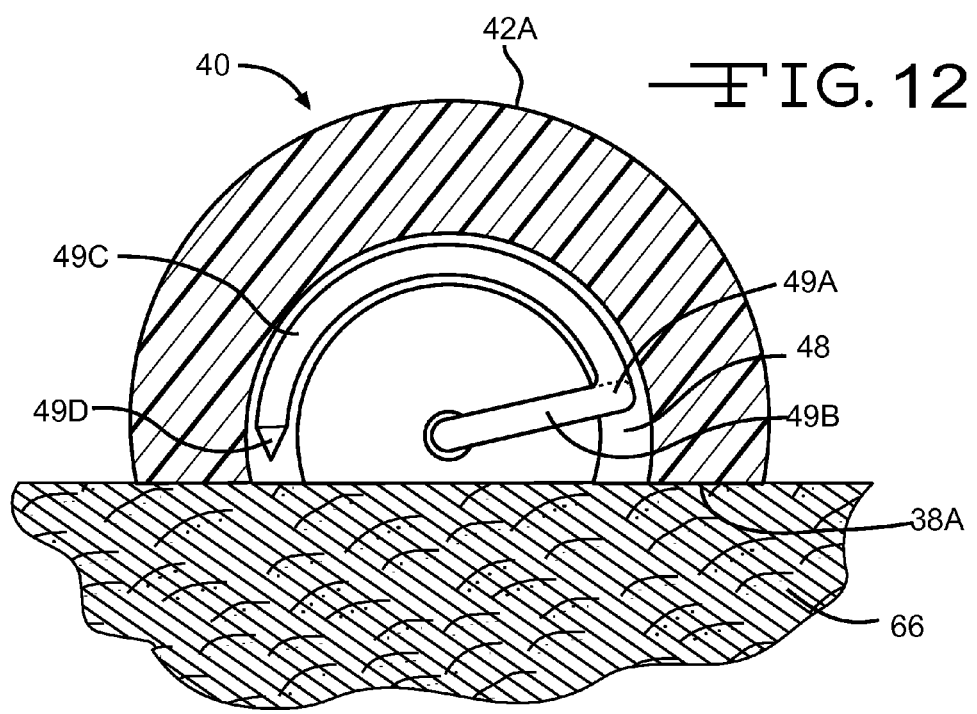
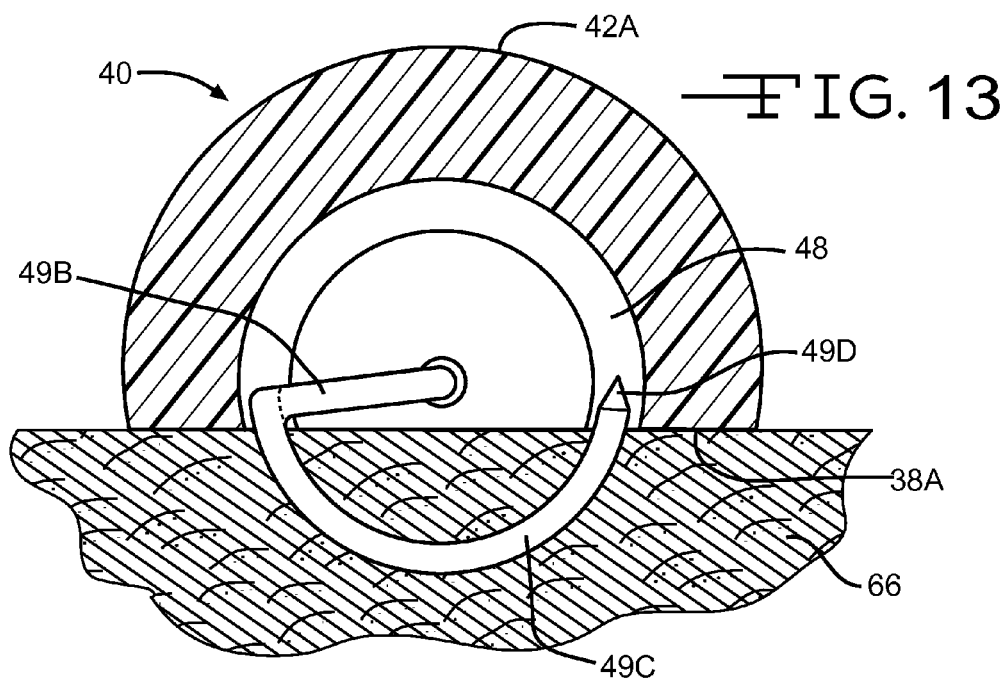

ANCHORING MECHANISM FOR AN IMPLANTABLE STIMULATION LEAD

CROSS-REFERENCE TO RELATED APPLICATION

The present application claims priority from U.S. Provisional Application Ser. No. 61/116,718, filed Nov. 21, 2008.

BACKGROUND OF THE INVENTION

1. Field of the Invention

The present invention is related generally to implantable medical electrical leads. More specifically, the present invention is related to implantable neurological leads.

2. Prior Art

Spinal cord and other neurological stimulations by electrical leads are used for many purposes, including pain masking. These electrical leads emit a voltage or current which mimics the body's electrical response and masks a patient's pain.

As such, these leads must be precisely placed near a specific nerve or series of nerves to provide the required therapy. It is therefore critical that the correct nerve or nerves are targeted and that the lead does not move once in place. Lead migration, defined as the undesirable movement of a lead in the body over time, causes the stimulation therapy to become ineffective. Additional surgery is therefore required to reposition the lead and correct the problem.

One such neurological electrical stimulation lead is the percutaneous lead, which is well suited for stimulating nerve tissue. A percutaneous lead is a relatively long, slender, cylindrical lead with a small diameter and a series of electrode bands that wrap around the outside surface. The relatively long length and small cylindrical diameter allow for easy and unimpeded access to the nerve tissue along the spinal column through a small incision in the body. The series of electrode bands are programmed to emit an electrical signal such as a voltage or current that provides pain relief by targeting a specific nerve or nerves. However, the long, slender, cylindrical construction of percutaneous leads which make them advantageous for intricate placement and unimpeded advancement about the tight confines of the spinal column also make them prone to movement and migration.

One such solution to prevent lead migration is a suture type of lead fixation device. As discussed in U.S. Pat. Nos. 5,843,146 and 6,473,654 to Cross and Chinn, respectively, implanted leads are secured through the use of sutures designed to tie the implanted lead to bodily tissue.

The problem is that the use of sutures is not ideal in securing the lead to delicate neurological tissue, which may easily tear. Furthermore, suturing neurological stimulation leads requires invasive surgery to gain access to the spinal column area, which would defeat the minimally invasive benefits of the percutaneous lead. In addition, sutures can make it difficult to easily move the stimulation lead to a new desired location. A physician would have to perform another invasive surgery to gain access to the spinal column area to remove the old sutures and re-suture the lead to the new location.

Helical screw anchoring mechanisms are another means of fixating implanted leads. Such mechanisms are disclosed in U.S. Pat. No. 6,711,443 and U.S. Patent application publication 2007/0299493, both to Osypka. Helical fixation mechanisms are primarily used in the placement of cardiac leads. This fixation mechanism is beneficial in cardiac applications since the strong fibrous tissue of the heart muscle captures and prevents the embedded helical structure from becoming unsecured.

Helical fixation mechanisms, however, are not ideal in securing a lead to neurological tissue. The drilling action of the helix destroys the delicate neurological tissue as it bores into the tissue. In addition, since neurological tissue is not as strong and fibrous as that of cardiac tissue, the helical structure would easily rip out of and damage the delicate neurological tissue.

Hook style lead anchoring mechanisms have also been developed to secure cardiac leads to heart tissue. Two previous hook type anchoring mechanisms have been disclosed in U.S. Pat. Nos. 4,858,623 and 5,871,532 by Bradshaw et al. and Schroeppel, respectively. However these specific prior art anchoring examples are not well suited for anchoring to delicate neurological tissue. They could easily be dislodged through movement as a patient goes about their daily activities. As stated in column 4, line 65 of the '623 patent, "a slight tug on the lead will cause the hook to rotate about its pivot point to a position beyond the tip, thereby allowing the lead to be withdrawn". Such inadvertent dislodgement could occur through the movement of a patient's spinal column as they move.

Accordingly, what is desired is a percutaneous neurostimulator lead with a fixation mechanism that provides long term secure anchoring, prevents inadvertent lead dislodgement, minimizes neurological tissue damage and does not compromise the minimally invasive benefits of the lead.

SUMMARY OF THE INVENTION

The present invention is broadly directed to an improved percutaneous lead anchoring mechanism that affords the physician long term secure lead anchoring stability, prevents inadvertent dislodgement and allows for precise anchor deployment control.

The improved anchoring mechanism, which is located in the anchor housing at the distal end of the neurological lead, comprises a curved sharpened hook that pierces the neurological tissue and secures the implanted lead in place.

Movement of the anchor hook is controlled by rotation of a removable stylet from outside a patient's body. The stylet is first inserted through the lead. The stylet shaft connects to a tine at a socket opening of the anchor housing. Rotation of the stylet causes the tine to rotate which, in turn, deploys the connected anchor hook from the housing. Once the anchor hook is fully deployed and the lead is securely attached to the neurological tissue, the stylet is removed.

Importantly, the stylet can be re-inserted into the socket of the housing at a later time to retract the anchor hook from the tissue. This means the lead can be moved to a new location without the need for invasive surgery. Once the lead is repositioned, the anchor hook is re-deployed again to secure the lead in place. This process can be repeated as many times as needed. The anchor hook, however, cannot be moved without rotation of the internal tine by the stylet. Therefore, inadvertent dislodgement of the anchor hook is prevented, which keeps the lead from migrating from its intended location.

The anchor housing, which contains the anchor deployment mechanism, is designed with a flat planar bottom surface meeting a curved sidewall and curved distal end. This shape allows for relatively easy and unimpeded insertion of the lead into the narrow confines adjacent to the spinal column. The bottom flat planar housing surface allows for the lead to be positioned in close proximity to the desired neurological nerve tissue. It is from this flat bottom surface of the housing that the hook emerges.

These and other aspects of the present invention will become more apparent to those skilled in the art by reference to the following description and the appended drawings.

BRIEF DESCRIPTION OF THE DRAWINGS

FIG. 1 is a perspective view of a prior art neurological stimulator lead 10.

FIG. 2 is a perspective view of the present invention comprising a neurological stimulator lead 20 with the anchor housing 40 and stylet 30.

FIG. 3 shows an elevated view of the anchor housing 40.

FIG. 3A shows a cross-sectional view taken along line 3A-3A of FIG. 3.

FIG. 4 shows an elevated view of the stimulator lead 20 plugged into the socket opening 37 of the anchor housing 40.

FIG. 4A shows a cross sectional view taken along line 4-4 of FIG. 4.

FIG. 4B illustrates as alternate embodiment for connecting the distal end 18B of the stylet 18 to the tine 49.

FIG. 9 shows a perspective view of the present invention that has been inserted in a catheter sheath 52.

FIG. 10 is an enlarged view of the indicated area in FIG. 9 showing the anchor housing 40 protruding from a catheter sheath 52.

FIG. 12 shows an enlarged, cross-sectional view taken along line 12-12 of FIG. 11 of the anchor housing 40 positioned next to neurological tissue 66 prior to deployment of the anchor hook 49.

FIG. 13 shows an enlarged, cross-sectional view taken along line 13-13 of FIG. 11 showing the anchor housing 40 attached to neurological tissue 66 after deployment of the anchor hook 49.

DETAILED DESCRIPTION OF THE PREFERRED EMBODIMENTS

Figure 11:
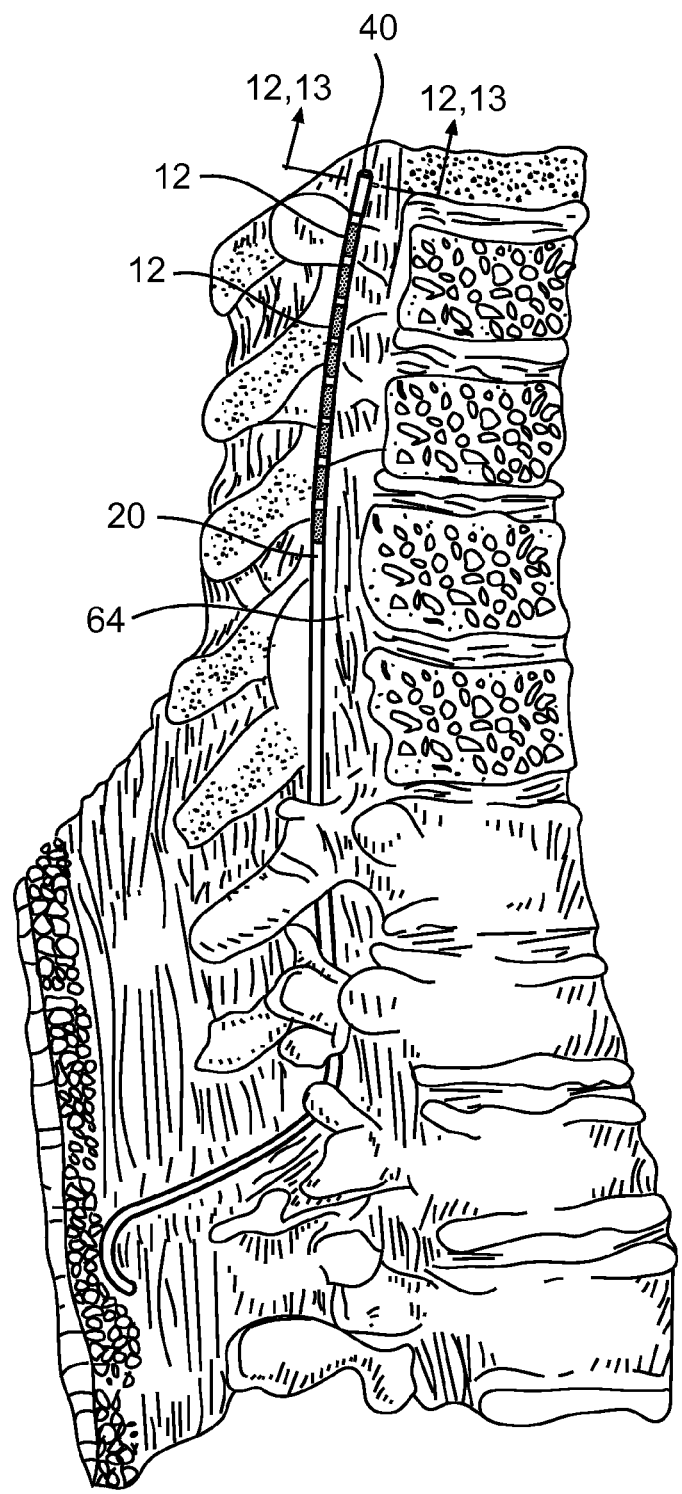
FIG. 11 shows a schematic view of the stimulation lead 20 of the present invention inserted in the spinal column 64 of a patient.

FIG. 1 is a generalized view of a prior art neurological stimulation lead 10. The lead 10 comprises a cylindrical lumen 16 with a series of proximal metal electrode bands 14 and a series of distal metal electrode bands 12. As those skilled in the art are readily aware, the proximal electrode bands 14 are designed to connect to the header (not shown) of an implantable medical device, for example, a cardiac pacemaker, a cardiac defibrillator, a neurostimulator, a drug pump, a bone growth stimulator, and the like. The distal electrode bands 12 are intended to be placed proximate body tissue, such as neurological tissue 66 (FIG. 13) comprising the spinal column system 64 (FIG. 11). That is for the purpose of providing electrical stimulation to the body tissue.

FIG. 2 illustrates the present invention neurological stimulation lead 20 with an anchoring housing 40 connected to the distal end thereof. As the illustration shows, the stimulation lead 20 has an elongate body comprising a sidewall 16 that extends from a proximal region 16A to a distal region 16B.

Within the proximal lead region 16A is a discrete series of metal electrode bands 14 that extend circumferentially around the outside surface thereof. The distal lead region 16B comprises a separate series of discrete metal electrode bands 12 that extend circumferentially around the lead sidewall 16. As is well known by those skilled in the art, the distal and proximal electrodes 12, 14 are electrically connected to each other by electrical conductors (not shown) extending along the lead body between respective ones of them. As will be described in greater detail hereinafter, an anchoring tine 49 (FIGS. 4, 6 to 8, 13 and 14) is contained within the anchor housing 40 connected to the distal lead region 16B.

The lead 20 has a hollow lumen 22 (FIGS. 4 and 4A) extending from its proximal region 16A to the distal region 16B. This lumen 22 is sized to receive a stylet 18 (FIG. 2) provided with a manipulatable handle 30 at its proximal end. In use, the stylet 18 is advanced through the lead lumen 22 to the anchor housing 40 where its distal end 18A connects to the tine 49 in a releasable engagement. Then, rotational movement of the stylet handle 30 causes the tine 49 to deploy from and retract into the anchor housing 40. This movement will be described in greater detail hereinafter.

FIG. 3 shows an enlarged view of the anchor housing 40. The anchor housing 40 is composed of a rigid biocompatible polymeric material, preferably of polyurethane. However, other polymeric materials not limited to polyethylene, polyether ether ketone, including silicone, and polyimide can also be used. In addition to polymeric materials, metals not limited to titanium, MP35N, platinum, niobium, gold, palladium, and their alloys can also be used to construct the anchor housing 40.

In that respect, the anchor housing 40 is preferably a molded member extending along a central longitudinal axis A-A and comprising a main housing portion 41 having a radiused sidewall 42 extending to a planar bottom surface 38 connected to a nose housing portion 43, also having a radiused sidewall 42A, extending to a curved nose 44 and a planar bottom surface 38A. Chamfers 42B, 42C (FIG. 5) are provided where the sidewalls 42, 42A and 44 meet the planar bottom surfaces 38, 38A.

The curved sidewalls 42, 42A and 44 of the housing 40 facilitate advancement of the lead 20 through the narrow confined passages of the spinal column with minimal interference. The planar bottom surfaces 38, 38A enable the anchor housing 40 to be placed in close proximity to the body tissue, such as neurological tissue to which the lead 20 will be anchored. A fin 38B protrudes from the bottom planar surface 38 at the proximal region of the main housing portion 41. With the lead 20 connected to the anchor housing 40 as shown in FIGS. 4 to 8, the fin 38B facilitates movement of the anchor housing 40/lead 20 assembly through body tissue without that portion of the lead adjacent to the planar bottom surface 38 snagging on body tissue.

The main housing portion 41 comprises a proximal end 35 having a lead opening 33 sized to receive the distal lead region 16B. The lead 16 is preferably secured in the position shown in FIGS. 2 and 4 to 8 by a suitable adhesive. The lead opening 33 in turn communicates with a housing channel 46 extending longitudinally through the main housing portion 41 to a tine passage 48.

The tine passage 48 communicates with a housing opening 41 where the main housing portion 41 connects to the nose housing portion 43. The tine passage 48 is a semi-circular passageway aligned perpendicular to the axis A-A within which the anchor tine 49 (FIG. 4) can freely rotate in an arcuate path. Tine passage 48 has a width extending along the longitudinal axis and communicates with the housing opening 41 having a similar width and located between the planar bottom surfaces 38, 38A of the main and nose housing portions 41, 43, respectively.

The housing channel 46 comprises a frusto-conical portion 46A extending distally from the lead opening 33 at the proximal housing end 35. The frusto-conical channel portion 46A tapers downwardly and inwardly to a distal channel portion 46B of a reduced diameter. The distal channel portion 46B communicated with the tine passage 48.

The anchor tine 49 comprises a proximal leg 49A that is preferably of a circular cross-section connected to a lateral portion 49B that connects to a distal, arc-shaped tine portion 49C. The arc-shaped tine portion 49C extends to a tine point 49D.

A sleeve 47 is connected to the proximal tine leg 49A. The sleeve is of a similar material as that of the tine 47. In an alternate embodiment, the sleeve 47 can be replaced by a bore drilled or otherwise provided in the proximal tine leg portion 49A. Either the sleeve 47 or the bore in the proximal tine portion provide a lumen into which the stylet 18 is received in a releasable friction fit relationship. The purpose of this relationship will be described in detail hereinafter.

To construct the anchor housing 40, the proximal tine leg 49A supporting the sleeve 47 is first received in the distal channel portion 46B while the lateral and distal, arc-shaped tine portions 49B, 49C are in the tine passage 48. Then, the nose housing portion 43 is secured to the main housing portion 41 at seam 41A (FIGS. 3 and 4). This serves to capture the tine 47 inside the housing. Tine 49 is preferably composed of a metallic or polymeric material and rotate freely (both clockwise and counter clockwise) inside the tine passage 48. The pointed tip 49D is designed to pierce through neurological tissue with minimal tissue damage.

The tine 49 and sleeve 47 are preferably composed of a biocompatible metal, preferably of titanium. Alternate metals that could also be used include, but are not limited to, the following: MP35N, nitinol, platinum, niobium, gold, palladium, and their alloys. Additionally rigid biocompatible polymers could be used to construct the tine 49 and sleeve 47. These materials include but are not limited to polyurethane, polyethylene, silicone, polyether ether ketone, and polyimide.

The length of the anchor housing 40 measured along the longitudinal axis A-A is from about 0.0125 inches to about 0.50 inches. The height of the anchor housing measured from the planar bottom surfaces 38, 38A to the apex of the radiused sidewalls 42, 42A is from about 0.01 inches to about 0.10 inches. The diameter of the sidewalls 42, 42A is measured from one edge of the planar bottom surfaces 38, 38A to the other perpendicular to the longitudinal axis A-A. This also defines the width of the planar bottom surfaces 38, 38A which are from about 0.02 inches to about 0.10 inches.

As shown in FIGS. 3 and 4, an inlet 42A is formed part way into the thickness of the sidewall 42 of the main housing portion 41. The inlet 42A is shaped and formed to receive the tongue 52A of a catheter sheath 52 (FIG. 10). That way, the inlet 42A helps align the sheath 52 with the anchor housing 42. While the inlet 42A is shown positioned on the top surface of the housing sidewall 42, that is only exemplary. Such an inlet 42A or a combination of multiple inlets could be positioned anywhere along the circumferential extent of the outer shell 42 to perform the function of receiving the catheter tongue 52A to align the sheath 52 with the lead 20 and anchor housing 40.

In use, the catheter 60 including the sheath 52 is first moved over the lead 20 until its tongue 52A is received in the inlet 42A provided in the sidewall 42 of the main housing portion 41. The stylet 18 is then moved through the lumen 16 in the lead 20 until the distal stylet end 18A is received in the lumen provided by the sleeve 47 or by the bore in the proximal tine portion 49A. The lumen in the sleeve 47 or the tine bore (not shown) is sized so that the distal end 18A of the stylet is received therein in a releasable friction fit relationship.

This assembly in then inserted into a body and advanced to a tissue of interest that is intended to be electrically stimulated or otherwise assisted in a beneficial manner. Once the target tissue has been reached, the stylet handle 30 is rotated in either a clockwise or counter clockwise manner. This causes the stylet 18 and the proximal leg 49A of the anchor tine 49 to rotate. As the tine 49 rotates, its arc-shaped portion 49C rotates along the tine passage 48. This movement causes the pointed tip 49D to pierce into body tissue situated proximate the planar anchor housing surfaces 38, 38A. Further rotational movement causes the tip 49D to move through an arc in the tissue and back into the housing opening 41. That way, the tine 49 pierces into and then out of body tissue, thereby preventing longitudinal movement of the lead 20 along the axis A-A of the housing 40. As this rotational movement takes place, the catheter 60 serves as a counter balance to prevent the lead 16 and anchor housing 40 from rotating along with the tine 49.

The stylet 18 is next removed from its engagement with the anchor housing by applying a slight tugging or pulling force on the handle 30. This is sufficient to separate the distal stylet end from its friction fit relationship with the proximal tine bore 49A. Finally, the tongue 52A of the catheter sheath 52 is removed from the inlet 42A in the anchor housing 40 and the sheath is completely removed from the body.

Figure 5:
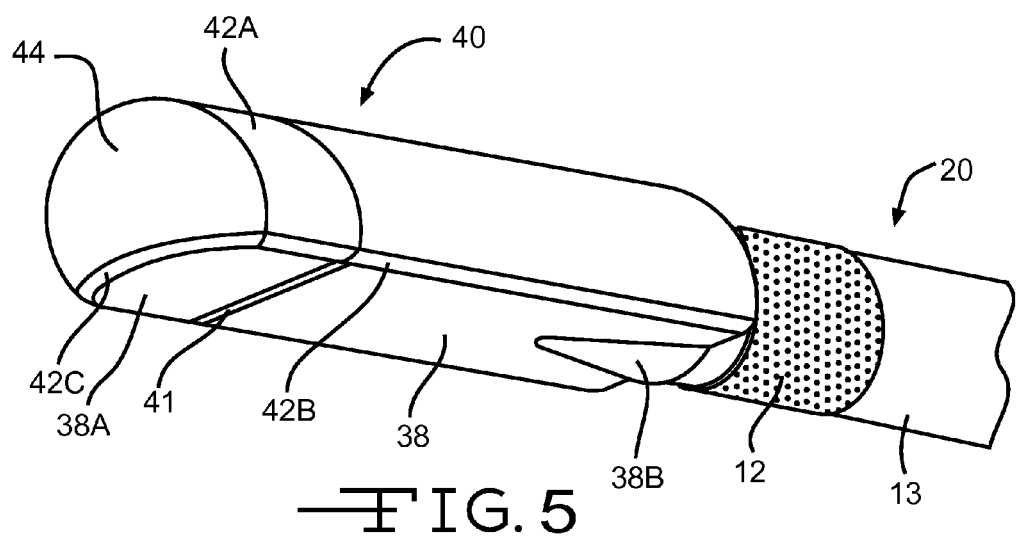
FIG. 5 is a perspective view of the lead 20 connected to the anchor housing 40 prior to deployment of the anchor hook 49.

FIG. 5 shows a perspective view of the distal-end of the present invention prior to deployment of the anchor hook 49 through the housing opening 41. Once the hook 49 is fully deployed and has pierced through the body tissue 66, the pointed tip 49D enters the opening 41 on the opposite side thereof. This ensures that the anchor hook 49 does not become dislodged from the tissue to which it is anchored.

Figure 6:
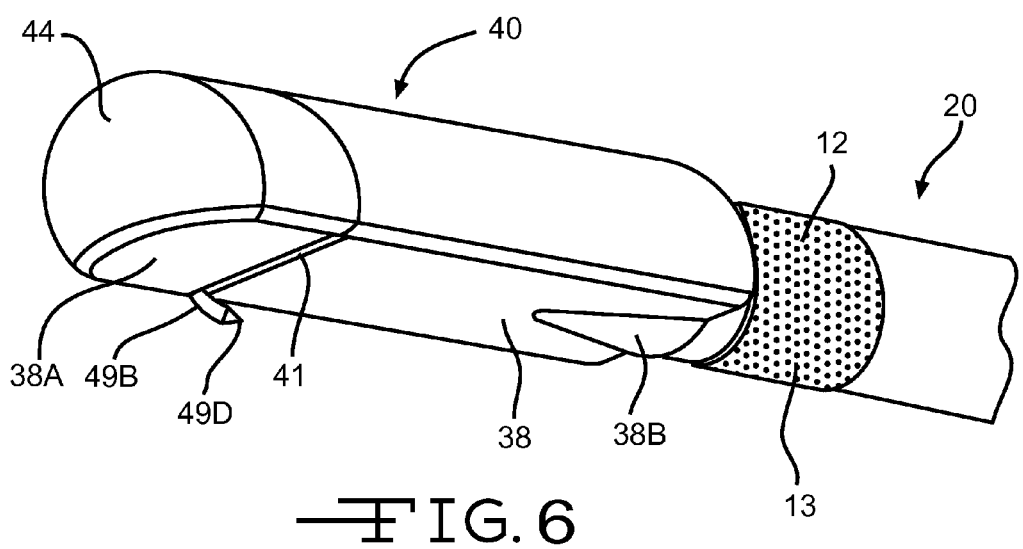
FIG. 6 is a perspective view of the lead 20 connected to the anchor housing 40 shown in FIG. 5 during initial deployment of the anchor hook 49.

FIG. 6 shows the anchor tine 49 beginning to emerge from the anchor housing 40 through the opening 41. The tine point 49 is just beginning to emerge from the housing 40.

Figure 7:
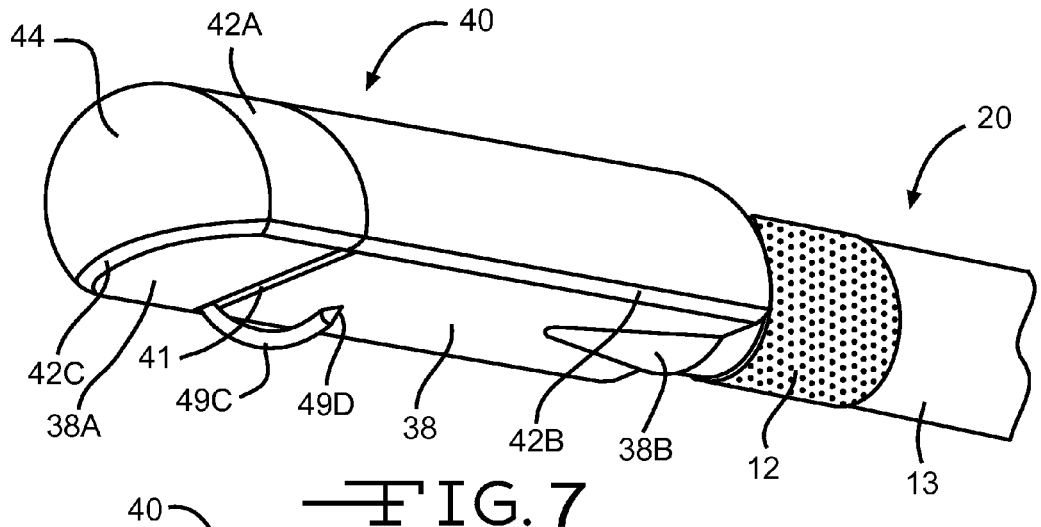
FIG. 7 is a perspective view of the anchor housing 40 midway through deployment of the anchor hook 49.

FIG. 7 shows the anchor tine 49 continuing to be deployed from the anchor housing 40 through the opening 41. As the illustration shows, the anchor tine 49 passes through an arcuate path.

Figure 7A:
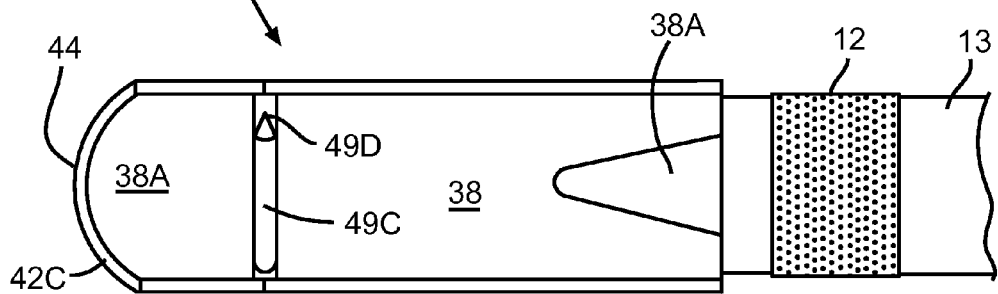
FIG. 7A is a bottom plan view of the anchor housing 40 shown in FIG. 7.

FIG. 7A shows the view of the emerging tine 49 from the perspective of the bottom planar surface 38A of the housing. One can see the opening 41 across the width of the bottom surface 38A.

Figure 8:
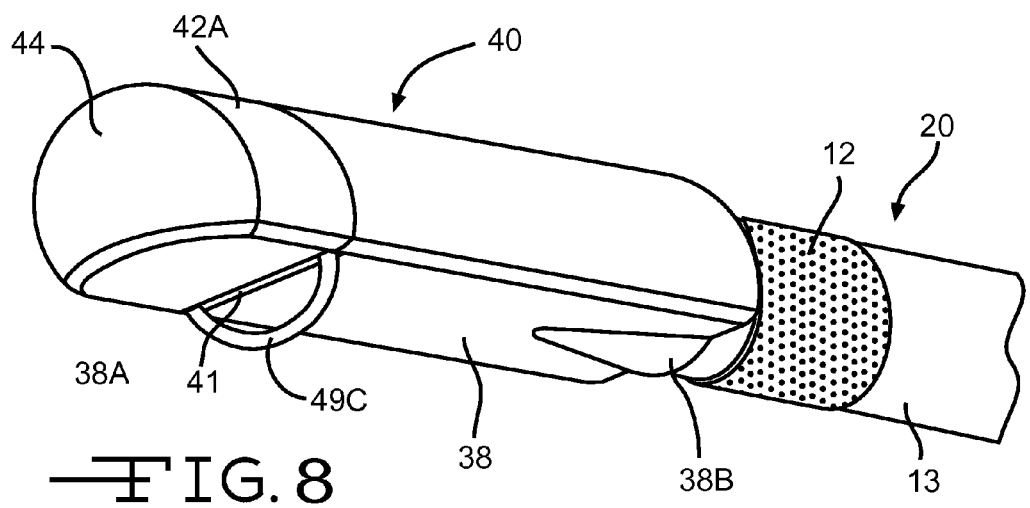
FIG. 8 is a perspective view of the anchor housing 40 shown in FIG. 6 with a fully deployed the anchor hook 49.

FIG. 8 shows the anchor tine 49 in a fully deployed position. The pointed tip 49D has traversed from the right side to the left side of the opening 41 and now resides back inside the housing 40.

FIG. 9 shows the present invention inserted through an implantation catheter 60 comprising a sheath 52 connected to a catheter handle 62. The stylet shaft 18 is shown inserted through the catheter handle 62 and catheter sheath 52.

FIG. 10 shows an enlarged view of the distal end of the sheath shown in FIG. 9. The smooth surface of the catheter sheath 52 is aligned with the anchor housing 40. The tongue 52A of the sheath 52 is aligned with the housing shell inlet 42A.

The neurological lead 20 is now ready for implantation into the spinal column of a patient. A minimally invasive incision is first cut into the patient and the neurological lead 20 which is encased in the catheter sheath 52 as shown in FIGS. 9 and 10, is inserted into the body through the incision. The catheter sheath 52 encased lead 20 is then advanced in the body to its intended location along the spinal column 64. The catheter handle 62 is used to steer the lead 20 into position.

FIG. 11 shows the neurological lead 20 in place and secured along the spinal column 64. The distal electrodes 12 are shown in close proximity to the spinal column 64.

FIG. 12 shows an exploded cross-sectional view of the housing 40 shown in FIG. 11 prior to deployment of the anchor hook 49. As FIG. 12 shows, the anchor housing 40 has been positioned adjacent to the neurological tissue 66. The flat planar bottom surface 38 of the hosing 40 allows the lead 20 to be positioned in close proximity to the targeted neurological tissue.

FIG. 13 shows an enlarged cross-sectional view of the anchor tine 49 in its fully deployed position. The pointed tip 49D of the tine 49 has pierced and penetrated through the adjacent body tissue 66. A portion of the tine 49 has completed its arc path through the tissue 66 and now resides in the opposite side of the tine 49. The tine 49 is locked into place with the tip 49D embedded in the body tissue. This prevents the tine 49 from becoming detached from the tissue 66.

An important aspect of the present invention is that the lead 20 can be removed from the body tissue. That may be because a new one is needed, or the present lead needs to be repositioned. In either case, the catheter 60 including the sheath 52 is moved over the lead 20 until the tongue 52A reengages the inlet 42A. The stylet 18 is moved through the proximal end 16A of the lead 20 until the distal stylet end 18A engages with the sleeve 47 or the bore provided in the proximal tine portion 49A. The stylet handle 30 is then rotated in an opposite direction to that used to originally secure the anchor housing to the body tissue. This serves to rotate the tine 49 out of the body tissue and back into the anchor housing. Once completely inside, the entire assembly including the lead 20 with the anchor housing 40, the catheter 60 and the stylet 18 can be removed completely from the body of move to a new location for redeployment.

FIG. 4B shows another aspect of the present invention is that the distal end 18A of the stylet need not necessarily connect to the tine 49 using the sleeve 47 or a bore in the tine. Instead, one of the distal stylet end 18A and the proximal tine portion 49A can have a Philips or standard-type end 18B that is received in a mating receptacle 47A provided in the other of them. That is in a similar manner as a screw driver and screw is connected to each other to insert a screw-type fastener into a piece of wood, and the like.

It is appreciated that various modifications to the inventive concepts described herein may be apparent to those of ordinary skill in the art without departing from the scope of the present invention as defined by the appended claims.

What is claimed is:

1. An implantable medical electrical lead, which comprises:
   a) an elongate lead body comprising a lead lumen extending from a proximal lead region to a distal lead region, wherein the proximal lead region is connectable to a medical device and the distal lead region has a distal lead opening of the lead lumen;
   b) an anchor housing connected to the distal lead region, the anchor housing comprising a proximal housing portion extending along a first longitudinal axis to a distal housing portion, wherein a housing channel in the anchor housing extends from a proximal channel portion having a proximal channel opening of a first diameter to a distal channel portion having a second diameter less than the first diameter, the proximal channel opening being in communication with the distal lead opening and the lead lumen;
   c) a tine positioned inside the housing channel and comprising a proximal tine portion extending to a distal tine portion terminating at a tine point, wherein the proximal tine portion comprises a tine lumen that is in open communication with the distal channel portion of the second diameter leading to the proximal channel opening of the first, greater diameter;
   d) wherein the tine is rotatable in a first direction along a plane perpendicular to the first longitudinal axis of the housing and out an opening in the housing to thereby deploy the tine point; and
   e) wherein the tine is rotatable in a second, opposite direction along the plane back into the housing opening to thereby retract the tine point.

2. The lead of claim 1 wherein the tine lumen is detachably connectable to a stylet moved through the lead and into the proximal channel opening and then the distal channel portion of the second diameter to connect to the tine in a releasable friction fit relationship for rotational movement thereof by rotating the stylet.

3. The lead of claim 1 wherein the housing has a curved sidewall meeting a planar bottom surface provided with the housing opening.

4. The lead of claim 1 wherein the proximal tine portion resides in the proximal channel portion of the housing and extends along the first longitudinal axis to a tine passage comprising the opening in the housing.

5. The lead of claim 4 wherein the tine passage has a semi circular cross-section perpendicular to the first longitudinal axis of the housing.

6. The lead of claim 1 wherein the proximal tine portion has a second longitudinal axis parallel to the first longitudinal axis of the housing.

7. The lead of claim 1 wherein the housing and tine are composed of a biocompatible metal or polymer material.

8. The lead of claim 1 wherein the distal tine portion is arc shaped.

9. The lead of claim 1 wherein the tine lumen is detachably connectable to a stylet moved through the lead and into the proximal channel opening and then the distal channel portion of the second diameter to connect to the tine at the tine lumen for rotational movement thereof by rotating the stylet, and wherein in response to rotational manipulation of a stylet connected to the tine at the tine lumen,
   i) the tine is rotatable in a first direction along the plane perpendicular to the first longitudinal axis of the housing and out the housing opening to thereby deploy the tine point, and
   ii) the tine is rotatable in a second, opposite direction along the plane back into the housing opening to thereby retract the tine point.

10. An implantable medical electrical lead, which comprises:
   a) an elongate lead body comprising a lead lumen extending from a proximal lead region to a distal lead region, wherein the proximal lead region is connectable to a medical device and the distal lead region has a distal lead opening of the lead lumen;
   b) an anchor housing connected to the distal lead region, the anchor housing comprising a proximal housing portion extending along a first longitudinal axis to a distal housing portion, wherein a housing channel in the anchor housing extends from a proximal channel portion having a proximal channel opening of a first area in cross-section perpendicular to the first longitudinal axis to a distal channel portion having a second area in cross-section perpendicular to the first longitudinal axis that is less than the first area, the proximal channel opening being in communication with the distal lead opening and the lead lumen;

c) a tine positioned inside the housing channel and comprising a proximal tine portion extending to a distal tine portion terminating at a tine point, wherein the proximal tine portion comprises a tine lumen that is in open communication with the distal channel portion of the second area leading to the proximal channel opening of the first, greater area;

d) wherein the tine is rotatable in a first direction along a plane perpendicular to the first longitudinal axis of the housing and out an opening in the housing to thereby deploy the tine point; and e) wherein the tine is rotatable in a second, opposite direction along the plane back into the housing opening to thereby retract the tine point.

11. The lead of claim 10 wherein the tine lumen is detachably connectable to a stylet moved through the lead and into the proximal channel opening and then the distal channel portion of the second area to connect to the tine at the tine lumen for rotational movement thereof by rotating the stylet, and wherein in response to rotational manipulation of stylet connected to the tine at the tine lumen, i) the tine is rotatable in a first direction along the plane perpendicular to the first longitudinal axis of the housing and out the housing opening to thereby deploy the tine point, and ii) the tine is rotatable in a second, opposite direction along the plane back into the housing opening to thereby retract the tine point.

12. The lead of claim 10 wherein the tine lumen is detachably connectable to a stylet moved through the lead and into the proximal channel opening and then the distal channel portion of the second diameter to connect to the tine in a releasable friction fit relationship for rotational movement thereof by rotating the stylet.

13. The lead of claim 10 wherein the housing has a curved sidewall meeting a planar bottom surface provided with the housing opening.

14. The lead of claim 10 wherein the proximal tine portion resides in the proximal channel portion of the housing and extends along the first longitudinal axis to a tine passage comprising the opening in the housing.

15. The lead of claim 14 wherein the tine passage has a semi circular cross-section perpendicular to the first longitudinal axis of the housing.

16. The lead of claim 10 wherein the proximal tine portion has a second longitudinal axis parallel to the first longitudinal axis of the housing.

17. The lead of claim 10 wherein the distal tine portion is arc shaped.

18. An anchor housing that is connectable to an implantable medical electrical lead, the anchor housing comprising:

a) a proximal housing portion extending along a first longitudinal axis to a distal housing portion, wherein a housing channel in the anchor housing extends from a proximal channel portion having a proximal channel opening of a first area in cross-section perpendicular to the first longitudinal axis to a distal channel portion having a second area in cross-section perpendicular to the first longitudinal axis that is less than the first area;

b) a tine positioned inside the housing channel and comprising a proximal tine portion extending to a distal tine portion terminating at a tine point, wherein the proximal tine portion comprises a tine lumen that is in open communication with the distal channel portion of the second area leading to the proximal channel opening of the first, greater area;

c) wherein the tine is rotatable in a first direction along a plane perpendicular to the first longitudinal axis of the housing and out an opening in the housing to thereby deploy the tine point; and d) wherein the tine is rotatable in a second, opposite direction along the plane back into the housing opening to thereby retract the tine point.

* * * * *